(12) United States Patent
Nguyen et al.

(10) Patent No.: US 6,344,206 B1
(45) Date of Patent: Feb. 5, 2002

(54) COMBINATION OF A RETINOID WITH A POLYAMINE POLYMER

(75) Inventors: Quang Lan Nguyen, Antony; Boudiaf Boussouira; Stephanie Prince, both of Paris; Paolo Giacomoni, Orsay, all of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/652,012

(22) Filed: Aug. 31, 2000

Related U.S. Application Data

(62) Division of application No. 09/085,839, filed on May 28, 1998.

(30) Foreign Application Priority Data

May 28, 1997 (FR) .............................. 97 06533

(51) Int. Cl.⁷ .......................... A61K 7/00; A61K 9/127; A61K 7/42; A61K 7/021
(52) U.S. Cl. ........................... 424/401; 424/59; 424/64; 424/450; 424/DIG. 16; 514/725; 514/773.3
(58) Field of Search .......................... 424/401, 59, 63, 424/64, 70.17, 78.03, DIG. 16; 514/772.3, 725, 938

(56) References Cited

U.S. PATENT DOCUMENTS

| | | | |
|---|---|---|---|
| 4,888,363 A | 12/1989 | Dulak et al. ................ | 514/725 |
| 4,997,649 A | 3/1991 | Papaconstantin et al. | 424/195.1 |
| 5,425,938 A | 6/1995 | Znaiden et al. ........... | 424/78.02 |
| 5,618,850 A * | 4/1997 | Coury et al. ............. | 514/772.2 |
| 5,879,688 A | 3/1999 | Coury et al. ................ | 424/401 |

FOREIGN PATENT DOCUMENTS

| | | |
|---|---|---|
| EP | 0 209 509 | 1/1987 |
| EP | 0 260 186 | 3/1988 |
| EP | 0 608 433 | 8/1994 |

OTHER PUBLICATIONS

Ana–Rosa Viguera et al; "A water–soluble Polylysine–Reinaldehyde Schiff Base. Stability in Aqueous and Nonaqueous Environments", *The Journal of Biological Chemistry*, vol. 265, No. 5, Feb. 1990, pp. 2527–2532, XP–002057413.

Chemical Abstracts, XP–002057414, AN 114:128811, Oct. 24, 1990.

* cited by examiner

*Primary Examiner*—Diana Dudash
*Assistant Examiner*—Alysia Berman
(74) *Attorney, Agent, or Firm*—Oblon, Spivak, McClelland, Maier & Neustadt, P.C.

(57) ABSTRACT

A composition comprising the combination of at least one retinoid selected from the group consisting of vitamin A (retinol) and the bioconvertible precursors of vitamin A and at least one polyamine polymer.

22 Claims, No Drawings

COMBINATION OF A RETINOID WITH A POLYAMINE POLYMER

This application is division of Ser. No. 09/085,839 May 28, 1998.

BACKGROUND OF THE INVENTION

1. Field of the Invention

The present invention relates to cosmetic and/or dermatological compositions, in particular compositions for use in skin care which comprise at least one compound of the retinoid family. More particularly, the present invention relates to stable compositions comprising at least one compound of the retinoid family and at least one polyamine polymer.

2. Description of the Background

Retinoid-based cosmetic and/or dermatological compositions have undergone a major development during the past few years. Among the retinoids, the use of retinoic acid in compositions for the treatment of acne is well-known.

However, other derivatives of the retinoid family are also useful, both for the treatment of acne, as well as for skin care. These derivatives in particular are useful in limiting, even eliminating, the effects of skin ageing which include wrinkles, wizened appearance, yellowing, loss of elasticity, roughness, dryness, and the appearance of marks which are the usual manifestations of skin ageing. These manifestations are all the more pronounced the more frequently the skin has been exposed to sunlight or the more the skin is particularly sensitive to exposure to UV radiation.

Thus, the effects of intrinsic ageing of the skin (linked to age) and of photoageing (due to exposure to sunlight) may be cumulative. The manifestations of ageing usually appear at an advanced age; however, their prevention should be undertaken from the onset of adulthood by appropriate care.

The treatment of the skin with derivatives of the retinoid family forms part of these preventive or curative treatments of the manifestations of ageing which are wrinkles, wizened skin, yellowing, loss of elasticity, roughness, dryness and marks.

Among the derivatives of the retinoid family, retinol, also known by the name of vitamin A, and the esterified derivatives of retinol are most particularly useful. Indeed, retinol is a natural endogenous constituent of the human body. It is well-tolerated on application to the skin up to levels which are much higher than retinoic acid. The esters of retinol are converted to retinol by the human body.

However, when they are introduced into a cosmetic or dermatological composition intended for topical application, retinol and its esters are rapidly degraded under the effect of light, oxygen, metal ions, oxidizing agents, water and in particular under the effect of increases in temperature. The thermal degradation of retinol has been the subject of a study published in J. Soc. Cosm. Chem. 46, 191–198 (July–August 1995).

Various combinations of retinol and other derivatives of the retinoid family with antioxidants are known, the retinoids having enhanced stability in these combinations.

WO 93/00085 describes W/O emulsions comprising retinol and a stabilizing system consisting of a chelating agent such as, for example, EDTA and an antioxidant which may be either a fat-soluble antioxidant such as butylated hydroxytoluene (BHT) or vitamin E, or a water-soluble antioxidant such as vitamin C. According to this disclosure, it is also possible to prepare W/O emulsions containing retinol stabilized by a system consisting of a fat-soluble antioxidant and a water-soluble antioxidant.

EP 0 608 433 describes compositions containing retinol and a stabilizer selected from chelating agents and polysaccharides, oils with an iodine number greater than 70, polyethylene (propylene) glycols, hydroxycarboxylic acid salts, neutral amino acid salts, fat-soluble antioxidants combined with EDTA and with a benzophenone, fat-soluble antioxidants combined with an acidic compound and with a benzophenone, cyclodextrin derivatives in which an antioxidant or a UV-screening agent is included, butanediol and/or fat-soluble antioxidants, water-soluble benzophenone derivatives, basic amino acids and their salts, acidic amino acids and their salts, polar oils and hydrophilic mineral clays.

The use of certain polyamine compounds as antioxidants is known as disclosed in EP 0 209 509.

However, none of the prior art compounds, whether they are described as an antioxidant or more specifically as a stabilizer for a retinoid, make it possible to satisfactorily stabilize retinoids which, therefore, is a continuing need in the art.

SUMMARY OF THE INVENTION

Accordingly, one object of the present invention is to provide a retinoid composition in which the retinoid is satisfactorily stabilized.

Briefly, this object and other objects of the present invention as hereinafter will become more readily apparent can be attained by a composition comprising the combination of:

(A) at least one retinoid selected from the group consisting of vitamin A (or retinol) and the bioconvertible precursors of vitamin A; and (B) at least one polyamine polymer selected from the group consisting of:
(A) a polyalkylenepolyamine or one of its derivatives selected from the group consisting of:
(i) polyakylenepolyamines;
(ii) alkylated derivatives of polyalkylenepolyamines (A) (i);
(iii) products of addition of alkylcarboxylic acids to the polyalkylenepolyamines (A) (i);
(iv) products of addition of ketones and of aldehydes to the polyalkylenepolyamines (A) (i);
(v) products of addition of isocyanates and of isothiocyanate to the polyalkylenepolyamines (A) (i);
(vi) products of addition of alkylene oxide or of polyalkylene oxide block polymers to the polyalkylenepolyamines (A) (i);
(vii) quaternized derivatives of polyalkylenepolyamines (A) (i);
(viii) products of addition of a silicone to the polyalkylenepolyamines (A) (i);
(ix) a copolymer of dicarboxylic acid and polyalkylenepolyamines (A) (i);
(B) polyvinylimidazoles;
(C) polyvinylpyridines;
(D) products of addition of 1-vinylimidazole monomers of formula (I):

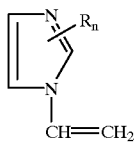

(I)

in which the R radicals, which are identical or different, represent H, or a linear or cyclic, saturated or unsaturated $C_1$–$C_6$ alkyl radical and n is an integer from 1–3, to the polyalkylenepolyamines (A)(i) to (A)(ix);

(E) polymer based on amino acids containing a basic side chain; and (F) cross-linked derivatives of the polymers (A)(i) ti (A) (ix), (B) (C) (D) and (E).

DETAILED DESCRIPTION OF THE PREFERRED EMBODIMENTS

It has now been found, surprisingly, that the combination of a retinoid selected from the group consisting of vitamin A (retinol) and the bioconvertible precursors of vitamin A with certain polyamine polymers make it possible to avoid the degradation, in particular the thermal degradation, of these retinoids. Thus, these retinoids can be introduced into cosmetic and/or dermatological compositions, and be stored for several months without impairment of their efficacy.

Vitamin A is to be understood as retinol of the all-trans type or of the 13-cis type.

The expression bioconvertible precursor of vitamin A means any compound which is capable of being converted into vitamin A by the human body. These compounds include retinol esters, in particular $C_1$–$C_{30}$ esters. Particularly preferred are the $C_1$–$C_6$ esters which are very rapidly degraded to retinol by the human body.

An aspect of the invention is also a cosmetic or dermatological composition comprising the combination as described above and at least one physiologically acceptable carrier.

Another aspect of the invention is the use of at least one polyamine polymer as defined above for enhancing the stability of a composition comprising a retinoid selected from vitamin A (or retinol) and the bioconvertible precursors of vitamin A.

Still another aspect of the invention is a process for enhancing the stability of a composition comprising a retinoid selected from vitamin A (or retinol) and the bioconvertible precursors of vitamin A, this process consisting in combining with the said retinoid an effective quantity of at least one polyamine polymer as defined above.

An effective quantity of a polyamine polymer is understood to mean a sufficient quantity to prepare a notable and significant improvement in the thermal stability of the retinoid (s) present in the composition. This minimum quantity of stabilizing agent may vary depending on the nature of the physiologically acceptable carrier selected for the composition, and can be determined without any difficulty by means of a test for measuring thermal stability such as that given in the examples below.

An embodiment of the invention is the use of the combination of at least one retinoid selected from vitamin A (or retinol) and the bioconvertible precursors of vitamin A and of at least one polyamine polymer in or for the preparation of a composition for dermatological treatment for combating, and/or for preventing irritation, inflammation, immunosuppression and/or acne.

Another embodiment of the invention is a Cosmetic process of combating the signs of ageing, particularly the signs of ageing which are induced by photoperoxidation, in particular the photoperoxidation of squalene and/or of collagen, by topical application to the skin and/or the scalp and/or the hair of a composition comprising at least one retinoid selected from vitamin A (or retinol) and the bioconvertible precursors of vitamin A and at least one polyamine polymer of the invention. Similarly the cosmetic composition is useful for combating and/or preventing the photoinduced signs of ageing of the skin and/or the hair, and in another embodiment, a dermatological composition which comprises a combination of the invention which combats the signs of ageing of the skin or of the hair, particularly the signs of ageing which are induced by photoperoxidation, in particular photoperoxidation of squalene and/or of collagen.

Other characteristics, aspects and advantages of the present invention will become evident upon consideration of the following:

Suitable polyamine polymers of the present invention include linear polymers, hyperbranched polymers and dendrimer forms.

The hyperbranched polymers are molecular constructions having a branched structure, in general around a core. Their structure, as a general rule, lacks symmetry. The basic units or monomers which serve for the construction of the hyperbranched polymer may be of different types and their distribution is irregular. The branches of the polymer may be of different types and lengths. The number of basic units, or monomers, may be different depending on the different branches. While being asymmetric, the hyperbranched polymers may have an extremely branched structure around a core; or may have successive layers or generations of branches; or a layer of terminal chains.

The hyperbranched polymers are generally derived by the polycondensation of one or more ABx monomers, A and B being reactive groups capable of reacting together, x being an integer greater than or equal to 2, but other processes of preparation may be employed. The hyperbranched polymers have a degree of polymerization DP=1−b, b being the percentage of nonterminal functionalities of B which have not reacted with the A group. The condensation being nonsystematic, in contrast to the synthesis of dendrimers, the degree of polymerization is less than 100%. Usually, by known methods of synthesis, DP is between 15 and 90%. It is possible to react a T terminal group with the hyperbranched polymer in order to obtain a particular functionality at the terminous of the chain. Such polymers are described in particular in B. I. Voit, Acta Polymer., 46, 87–99 (1995); EP 0 682 059; WO 96/14346; WO 96/14345; WO 96/12754.

Several hyperbranched polymers may be combined with each other through a covalent bond or another type of bond, by means of their terminal groups. Such so-called "bridged" polymers are within the definition of the hyperbranched polymers of the present invention.

Dendrimers are highly branched polymers and oligomers which are also known and have a well-defined chemical structure. It is said that they are "perfect" hyperbranched polymers. As a general rule, dendrimers comprise a core, a defined number of generations of branches, or spindles, and terminal groups. The generations of spindles consist of structural units which are identical for the same generation of spindles and which may be identical or different for different generations of spindles. The generations of spindles extend radially in a geometric progression from the core. The terminal groups of a dendrimer of the Nth generation are terminal functional groups of the spindles of the Nth generation or terminal generation. Such polymers are described in particular in D. A. Tomalia, A. M. Naylor and W. A. Goddard III, *Angewandte Chemie, Int. Ed. Eng.* 29, 138–175 (1990); C. J. Hawker and J. M. J. Frechet, *J. Am. Chem. Soc.*, 112, 7638 (1990); B. I. Voit, Acta Polymer., 46, 87–99 (1995); N. Ardoin and D. Astruc, Bull. Soc. Chim. Fr. 132, 875–909 (1995).

Dendrimers can also be defined more particularly by the formula (DI):

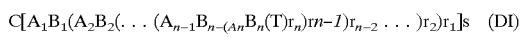

wherein:

C represents the core, linked by a number s of functionalities to s spindles $A_1B_1$ by means of $A_1$ groups;

s is an integer greater than or equal to 1 and less than or equal to the number of functionalities of C;

the index i (i=1, 2 ... n) is an integer which designates the generation of each spindle;

$r_i$ (i=1, 2 ... n−1) represents the number of functionalities of the group $B_i$ belonging to the spindle ($A_iB_i$), $r_i$ being an integer greater than or equal to 2;

for each spindle ($A_iB_i$) (i=1, 2 ... n), the group $B_i$ is linked to $r_i$ groups $A_{i+1}$ of a spindle ($A_{i+1}B_{i+1}$);

each group $A_i$ (i≧2) is linked to a single group $B_{i-1}$ of the spindle ($A_{i-1}B_{i-1}$);

the spindle of nth generation $A_nB_n$ is chemically linked to a number $r_n$ of T terminal groups, $r_n$ being an integer greater than or equal to zero.

The definition of dendrimers given above includes molecules containing symmetric branches; it also includes non-symmetric branch-containing molecules such as, for example, the dendrimers whose spindles are lysine groups, in which the branching of one generation of spindles on the preceding one occurs on the α and ε amines of the lysine, leading to a difference in the length of the spindles of the different branches.

Dense star polymers, starburst polymers and rod-shaped dendrimers are included in the present definition of dendrimers. The molecules called arborols and cascade molecules also fall within the definition of the dendrimers of the present invention.

Several dendrimers can be combined with each other, via a covalent bond or another type of bond, by means of their terminal groups to give entities known by the name of "bridged dendrimers" or "dendrimer aggregates". Such entities are included in the definition of the dendrimers of the present invention.

Dendrimers may be in the form of a group of molecules of the same generation, so-called monodisperse groups. The dendrimers may also be in the form of so-called polydisperse groups of different generations. The definition of the dendrimers of the present invention includes both the monodisperse and polydisperse groups of dendrimers.

Reference may be made to the following documents in which dendrimers comprising amine functional groups are described, the content of only the U.S. patent documents hereby being incorporated by way of reference into the specification: U.S. Pat. No. 4,694,064; U.S. Pat. No. 4,631,337; U.S. Pat. No. 5,530,092 (WO 95/02008); U.S. Pat. No. 5,610,268 (WO 93/14147); U.S. Pat. No. 4,360,646; Proc. Natl. Acad. Sci. USA, 85, 5409–5413 (1988).

The hyperbranched polymers and the dendrimers containing amine functional groups may also consist of a core and of generations of basic units, monomers or spindles, of any type, onto which a T terminal group carrying an amine functional group has been grafted.

The polyamine polymers (A)(i) to (A)(ix), (B), (C), (D), (E) and (F) of the invention are described in greater detail as follows:

(A)(i) The polyalkylenepolyamines preferably are polymers containing from 7–20,000 repeating units. Preferably, polyalkylenepolyamines are selected which comprise at least 5% of tertiary amines, advantageously at least 10% of tertiary amine functional groups, and still more preferably at least 20% of the amines. These polymers may be homopolymers or copolymers of linear, branched or dendrimeric structure.

These polymers comprise the following repeating units:

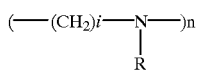

in which:

i represents an integer greater than or equal to 2, preferably i=2;

n represents an integer; and

R represents H or a unit

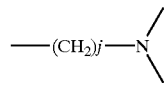

in which j represents an integer greater than or equal to 2, preferably j=2.

Products of the polyalkylenepolyamine family, which are also called polyaziridines, include in particular:

polyethyleneimine, which is a hyperbranched polymer well-known to those of skill in the art. Such polyethyleneimines, in particular, are described in: "KIRK-OTHMER ENCYCLOPEDIA OF CHEMICAL TECHNOLOGY", 3rd Edition, Vol. 20, 1982, p.214–216 and "Polyethyleneimine Prospective Application", H. N. Feigenbaum, Cosmetic & Toiletries, 108, 1993, p.73. The polyethyleneimine is commercially available from the company BASF under the tradenames LUPASOL or POLYIMIN; the polyethyleneimine is usually within an average molecular weight range of from 500–2,000,000.

Polyethyleneimines and polypropyleneimines in the form of denarimers, manufactured by the company DSM, are also known. U.S. Pat. No. 5,530,092 (WO 95/02008) and U.S. Pat. No. 5,610,268 (WO 93/14147), hereby incorporated by reference, describe polyalkylenepolyamines of the family of dendrimers as well as a process for their preparation.

(A)(ii) The alkylated derivatives of polyalkylenepolyamine are products which are well-known to those of skill in the art. They are obtained in a known manner by alkylation, in an aqueous or alcoholic medium, in the presence of an alkylating agent, preferably in the presence of NaOH, KOH or carbonate, at temperatures preferably ranging from 40–130° C.

The alkylating agent may be selected, for example, from derivatives of $C_1$–$C_8$ alkyl sulphate or a $C_1$–$C_8$ alkyl halide such as, for example, dimethylsulphate, diethylsulphate, butylbromide, hexylbromide, 2-ethylhexyl bromide, n-octylbromide or the corresponding chlorides. Reference can, for example, be made to DE 3743744 which describes the preparation of such products.

(A)(iii) The products of addition of alkylcarboxylic acids to polyalkylenepolyamines are products which are known to those of skill in the art and whose preparation is described, for example, in U.S. Pat. No. 5,641,855 (WO 94/14873), WO 94/20681 and U.S. Pat. No. 5,536,370 (WO 94/12560). The addition of alkylcarboxylic acids to polyalkylenepolyamines may be conducted by reacting, in a known manner, an acid, an amide, an ester, an acid halide with the polyalkylenepolyamine polymer.

The products of addition of alkylcarboxylic acids to polyalkylenepolyamines may be, for example, the products of addition of linear or branched, saturated or unsaturated $C_2$–$C_{30}$ alkylcarboxylic acids to a polyethyleneimine. Suitable carboxylic acids include acetic acid, propionic acid, butyric acid, 2-ethylhexanoic acid, benzoic acid, lauric acid, myristic acid, palmitic acid, stearic acid, oleic acid, linoleic acid, arachidonic acid, behenic acid, as well as mixtures of fatty substances, such as for example mixtures of fatty esters which are available in the form of natural It products, which include coconut oil, soyabean oil, linseed oil and rapeseed oil.

(A)(iv) The products of addition of ketones and of aldehydes to the polyalkylenepolyamines (A)(i) may be prepared by processes known to the is skilled artisan and lead to the production of α-hydroxyamine units.

(A)(v) The products of addition of isocyanates and of isothiocyanates to the polyalkylenepolyamines (A)(i) can be prepared by processes known to skilled artisan and lead to the production of urea and thiourea units.

(A)(vi) The products Of addition of alkylene oxide or of polyalkylene oxide block polymers to the polyalkylenepolyamines (A)(i) can be prepared by processes known to those of skill in the art. Reference is made to, for example, EP-541018 and U.S. Pat. No. 4,144,123, in which such molecules are described. Ethoxylated derivatives of polyethyleneimine are commercially available under the tradename: LUPASOL 61 (BASF).

(A)(vii) The quaternized derivatives of polyalkylenepolyamines (A)(i) can be prepared by processes known to those of skill in the art.

(A)(viii) The products of addition of a silicone to the polyalkylenepolyamines (A)(i) are, for example, polyethyleneimines having polydimethylsiloxane units grafted thereto whose preparation is described in U.S. Pat. No. 5,556,616 and marketed by the company MAC INTYRE under the tradename MACKAMER PAVS.

(A)(ix) The copolymers of dicarboxylic acid and polyalkylenepolyamines (A)(i) can be prepared by polycondensation of dicarboxylic acids with polyalkylenepolyamines.

Suitable dicarboxylic acids for the production of the polyamidoamines include the $C_2$–$C_{10}$ dicarboxylic acids such as, for example, oxalic acid, malonic acid, itaconic acid, succinic acid, maleic acid, adipic acid, glutaric acid, sebacic acid, terephthalic acid, ortho-phthalic acid, and mixtures thereof.

The polyalkylenepolyamines employed for the preparation of the polyamidoamines are advantageously selected from those having from 3–10 nitrogen atoms such as diethylenetriamine, triethylenetetraamine, dipropylenetriamine, tripropylene tetraamine, dihexamethylenetriamine, aminopropylethylene diamine, bis-aminopropylethylene diamine, as well as mixtures thereof. It is also possible to use polyethyleneimines as described above for the preparation of polyamidoamines. Such compounds are described, for example, in U.S. Pat. No. 4,144,423 and 5,677,384 (WO 94/29422), hereby incorporated by reference into the application.

(B) The term polyvinylimidazole comprises the polyvinylimidazole (PVI) homopolymers and copolymers obtained by radical polymerization of the vinylimidazole monomers of the following structure:

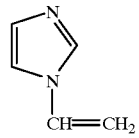

The vinylimidazole copolymers may comprise at least 5% of vinylimidazole units with monomers selected from the vinylpyrrolidinone, acrylic acid and acrylamide. The synthesis of such compounds is well-known to those of skill in the art. In this regard, reference is made, in particular, to J. Am. Chem. Soc., Vol. 8, 1962, p.951; Polymer Letters Ed., Vol. 11, 1973, p.465–469; Macromolecules, Vol. 6(2), 1973, p.163–168; Ann. N. Y. Acad. Sci., Vol. 1, 1969, p.431; FR-A-1,477,147; JP-69 07395; J. Macromol. *Scien. Chem.*, Vol. A21(2), 1984, p.253.

(C) The term polyvinylpyridine comprises the vinylpyridine homopolymers and copolymers prepared by radical polymerization of the vinylpyridine monomers (substituted at the 2- or 4-position of the pyridine ring) of the following structure:

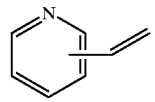

The vinylpyridine copolymers may comprise at least 5% of vinylpyridine units with monomers selected from the units vinylpyrrolidinone, acrylic acid and acrylamide.

(D) The products of addition of 1-vinylimidazole monomers of the formula (I):

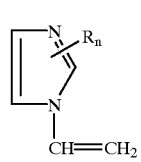

(I)

wherein the R radicals, which are identical or different, represent H, or a linear or cyclic, saturated or unsaturated, $C_1$–$C_6$ alkyl radical, n is an integer ranging from 1–3 to the polyalkylenepolyamines and their derivatives (A)(i) to (A)(ix).

Suitable derivatives of formula (I) include 2-methyl-1-vinylimidazole and 2-benzyl-1-vinylimidazole.

These products are known to those of skill and their preparation is described, for example, in U.S. Pat. No. 5,677,384 (WO 94/29422), hereby incorporated by reference into the application.

(E) The polymers based on amino acids containing a basic side chain are preferably selected from proteins and peptides comprising at least 5%, advantageously at least lot of amino acids selected from histidine, lysine and arginine.

Suitable such polymers include, for example, the polylysines and the polyhistidines.

(F) The cross-linked derivatives of polymers (A)(i) to (A)(ix), (B), (C) and (D). Suitable cross-linking agents include halohydrin, glycidyl, aziridino and isocyanate derivatives. Such cross-linking agents, as well as their methods of use, are well-known to those of skill in the art. Among the best known, are epichlorohydrin, $\alpha,\omega$-bis(chlorohydrin)polyalkylene glycol ethers, $\alpha,\omega$-dichloroalkanes such as, for example, 1,2-dichloroethane, 1,2-dichloropropane, 1,3-dichloropropane, 1,4-dichlorobutane and 1,6-dichlorohexane. These cross-linking agents and their use for cross-linking polyethyleneimine derivatives are described in U.S. Pat. No. 5,563,370 (WO 94/12560), hereby incorporated by reference into the application.

Preferably, polyamine polymers comprise at least 5% of tertiary amines, advantageously at least 10% of tertiary amine functional groups, and still more preferably at least 20% of such groups, are selected for conducting the present invention.

According to the invention, the polyamine polymer is advantageously selected from:

(A)(i) hyperbranched polyethyleneimines,
   (ii) alkylated derivatives of polyethylanniming.
   (iii) products of addition of alkylcarboxylic acids to polyethyleneimine;
   (iv) products of addition of ketones and of aldehydes to polyethyleneimine;
   (v) products of addition of isocyanates and of isothiocyanates to polyethyleneimine;
   (vi) products of addition of alkylene oxide or of polyalkylene oxide block polymers to polyethyleneimine;
   (vii) quaternized derivatives of polyethyleneimine;
   (viii) products of addition of a silicone to polyethyleneimine;
   (ix) copolymers of dicarboxylic acid and of polyethyleneimine;
(B) polyvinylimidazoles.

Still more preferably, the polyamine polymer is selected from:

(A)(i) Hyperbranched polyethyleneimines. Preferably, polyethyleneimines are selected which comprise at least 5% of tertiary amines, advantageously at least 10% of tertiary amine functional groups, and still more preferably at least 20%.

Those of skill in the art will know, by simple tests, how to adjust the relative proportion of retinoid and of polyamine polymer in order to obtain the desired effect. Indeed, the optimum proportions of the different constituents can vary, for example, according to the molecular weight of the polymer, the level of amines and/or the level of tertiary amines in this polymer.

In addition to the retinoid and the polyamine polymer, the combination according to the invention advantageously comprises at least one sunscreening agent. The addition of a sunscreening agent to the composition makes it possible to reinforce the stability of the combination of the retinoid with the polyamine polymer, while limiting the damaging action of UV radiation on the retinoid. Such a constituent may be selected from the known families of hydrophilic and lipophilic sunscreening agents active in UVA and/or UVB. These agents include, for example, cinnamic derivatives, such as 2-ethylhexyl p-methoxycinnamate; salicylic derivatives such as 2-ethylhexyl salicylate and homomenthyl salicylateo camphor derivatives such as, for example, 3-(4-methylbenzylidene)camphor; triazine derivatives such as 2,4,6-tris[p-(2'ethylhexyl-1'-oxycarbonyl)anilino]-1,3,5-triazine; benzophenone derivatives such as 2-hydroxy-4-methoxybenzophenone; dibenzoylmethane derivatives such as 4-tert-butyl-4'-methoxydibenzoylmethane; $\beta,\beta$-diphenylacrylate derivatives such as 2-ethylhexyl $\alpha$-cyano-$\alpha,\alpha$-diphenylacrylate; p-aminobenzoic acid derivatives such as octyl para-dimethylaminobenzoate; menthyl anthranilate; the screening polymers and screening silicones described in Application WO 93/04665; the hydrophilic screening agents containing at least one sulphonic —$SO_3H$ radical such as 2-phenylbenzimidazole-5-sulphonic acid or 1,4-benzenedi (3-methylidene-10-camphorsulphonic acid.

It is also possible to incorporate into the combination f the invention another compound known in the prior art as a retinol stabilizer. Suitable such compounds include chelating agents and polysaccharides, oils having an iodine number greater than or equal to 70, polyethylene glycol and/or polypropylene glycols, hydroxycarboxylates, amino acids and their salts, antioxidants such as butylated hydroxytoluene, butylated hydroxyanisole, $\alpha$-, $\beta$-, $\gamma$- and $\delta$-tocopherols, nordihydrogaiaretin, propyl gallate, esters of fatty acids and of vitamin C, ascorbic acid, ascorbic acid salts, isoascorbic acid, isoascorbic acid salts, sorbic acid, sorbic acid salts, butanediol, fatty acid and pentaerythritol esters, fatty esters of trimethylolpropane, and hydrophilic mineral clays. Such compounds are known as stabilizers of retinoids as disclosed in EP 0 608 433.

In the specific case of the treatment of acne, it is also possible to incorporate into the combination of the invention, advantageously, at least one specific anti-acne agent, one antiaeborrhoeic agent and/or one antibacterial agent, and in particular piroctone olamine marketed under the name octopirox by HOECHST.

In the compositions of the invention, the retinoid is preferably introduced in a quantity ranging from 0.0001–10% by weight relative to the total weight of the composition, advantageously from 0.001–3%, still more preferably from 0.01–1%.

In the compositions of the invention, the polyamine polymer is preferably introduced in a quantity ranging from 0.001–20% by weight relative to the total weight of the composition, advantageously from 0.1–10%.

The compositions of the invention may comprise, in addition, cosmetic or dermatological adjuvants selected from fatty substances, organic solvents, emulsifiers, nonionic thickeners, emollients, antioxidants, opacifiers, stabilizers, silicones, antifoaming agents, moisturizing agents, vitamins, perfumes, preservatives, surfactants, preferably nonionic, fillers, sequestrants, polymers other than those described above, propellants, alkalinizing or acidifying agents, colorants, or any other ingredient customarily used in cosmetics.

The fatty substances may consist of an oil or a wax or a mixture thereof, petroleum jelly, paraffin, lanolin, hydrogenated lanolin, acetylated lanolin. They also comprise fatty acids; fatty alcohols such as lauryl, cetyl, myristyl, stearyl, palmityl or oleyl alcohol, as well as 2-octyldodecanol; fatty acid esters such as glycerol monostearate, polyethylene glycol monostearate, isopropyl myristate, isopropyl adipate, isopropyl palmitate, octyl palmitate; $C_{12}$–$C_{15}$ fatty alcohol benzoates (Finsolv TN from FINETEX); polyoxypropylenated myristyl alcohol containing 3 moles of propylene oxide (WITCONOL APM from WITCO), and $C_6$–$C_{18}$ fatty acid triglycerides such as caprylic/capric acid triglycerides.

The oils which can be used in the present invention include vison oil, turtle oil, soyabean oil, grapeseed oil, sesame oil, maize oil, rapeseed oil, sunflower oil, cottonseed oil, avocado oil, olive oil, castor oil, jojoba oil, groundnut oil, hydrocarbon oils such as paraffin oils, squalane, petroleum jelly; esters such as isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, 2-diethylhexyl succinate, diisostearyl malate, 2-octyldodecyl lactate, glycerin triisostearate; silicone oils such as polymethylsiloxanes, polymethylphenylsiloxanes, polysiloxanes modified with fatty acids, polysiloxanes modified with fatty alcohols, polysiloxanes modified with polyoxyalkylenes, fluorinated silicones; perfluorinated and/or organofluorinated oils; higher fatty acids such as myristic acid, capric acid, caprylic acid, palmitic acid, stearic acid, behenic acid, oleic acid, linoleic acid, linolenic acid, isostearic acid, higher fatty alcohols such as cetanol, stearyl alcohol, oleyl alcohol.

The waxes may be selected from animal, plant, mineral and synthetic waxes. Suitable animal waxes include, in particular, beeswaxes and whale wax. Suitable plant waxes include, inter alia, Carnauba, Candelilla and Ouricoury waxes, cork fibre waxes, sugarcane waxes and Japan waxes. Suitable mineral waxes include, in particular, paraffin waxes, lanolin, microcrystalline waxes, lignite waxes and ozokerites. Suitable synthetic waxes include, in particular, polyethylene waxes and the waxes obtained by Fisher-Tropsch synthesis. All these waxes are well-known to those of skill in the art.

Suitable organic solvents include the lower alcohols and polyols such as ethanol, isopropanol, propylene glycol, glycerin and sorbitol.

The thickeners, preferably nonionic, may be selected from guar gums and celluloses, modified or otherwise, such as hydroxypropylated guar gum, cotylhdroxyethyl cellulose, silicas such as, for example, Bentone Gel MiO sold by NL INDUSTRIES, and Veegum Ultra sold by POLYPLASTIC.

Of course, those of skill in the art will be careful to select this or these optional additional compound and/or their quantities so that the advantageous properties intrinsically linked to the composition of the invention are not, or not substantially, altered by the addition(s) envisaged.

The compositions of the invention may be formulated as a lotion, a gel, a water-in-oil emulsion, an oil-in-water emulsion, or a triple emulsion. They may also be in a vectorized form, such as, for example, in the form of nanocapsules, liposomes, nanoemulsions or oleosomes.

These compositions are intended for application to the skin of the body, in particular the skin of the face and hands, to the mucous membranes and the semi-mucous membranes, and alternatively to the hair.

Such compositions may be in the form of care or make-up products. In particular, they maybe provided in the form of a care cream, a milk, a tonic, a cleansing and/or make-up removing product, a pack, a peeling product, an exfoliating agent, a sun protection product, a foundation, a tinted cream or a lipstick.

Having now generally described the invention, a further understanding can be obtained by reference to certain specific examples which are provided herein for purpose of illustration only and are not intended to be limiting unless otherwise specified.

In the examples and comparative examples, the percentages are given by weight of a given constituent relative to the volume of solvent (w/v), unless otherwise stated.

EXAMPLES

In the tests described below, polyethyleneimine (PEI) having a molecular weight 700 has been used which is marketed by Aldrich.

Test of Stability

The stability of a retinoid is defined in accordance with the present invention by the percentage of retinoid which remains in its original form after the composition containing the retinoid has been stored for a given period and at a given temperature.

A composition intended for commercial use should have a stability of at least 80% of the active form of the retinoid which it contains after 20 days of storage at 50° C.

TESTS

Test of Stability of All-trans-retinol at 0.3% in Ethanol During Preservation at 50° C.

The study conditions are the following:

PEI at 0.25, 0.5 and 1% (by weight/volume) in ethanol;

All-trans-retinol marketed by Fluka at 0.3% (by weight/volume) in ethanol;

Aerobic medium with 55 vol % air and 45 vol % ethanol;

Preservation at 50° C. in an oven;

The degradation of retinol under these conditions reaches nearly 99% in 20 days of storage at 50° C. The conditions under which the compositions were stored are particularly severe.

The following combinations are tested under the following conditions:

| Test 1: Measurement of the PEI dose effect | | | | |
|---|---|---|---|---|
| Constituents | Formula A1 | Formula B1 | Formula C1 | Formula D1 |
| All-trans-retinol Fluka (W/V) | 0.3% | 0.3% | 0.3% | 0.3% |
| PEI-700 Aldrich (W/V) | 0 | 0.25% | 0.5% | 1% |
| Absolute ethanol in ml | 100 | 100 | 100 | 100 |

The level of residual retinol after one month of preservation at 50° C. in an aerobic medium (55% of volume of air) is monitored by HPLC (on a Spherisorb ODS1 C18 column) by elution with an $H_2O/CH_3CO_2H/CH_3CO_2NH_4$/acetonitrile:

15/1/0.4/83.6 mixture.

The following results are obtained:

| Formula | Level of residual retinol |
|---|---|
| Formula A1 | 0% |
| Formula B1 | 88% |
| Formula C1 | 90% |
| Formula D1 | 91% |

Test 2: Comparison PEI, butylated hydroxytoluene (BHT) and tocopherols

| Constituents | Formula A2 | Formula B2 | Formula C2 | Formula D2 |
|---|---|---|---|---|
| All-trans-retinol Fluka (W/V) | 0.3% | 0.3% | 0.3% | 0.3% |
| PEI-700 Aldrich (W/V) | — | 0.25% | — | — |
| BHT (W/V) | — | — | 0.25% | — |
| α-Tocopherol (W/V) | — | — | — | 0.25% |
| Absolute ethanol in ml | 100 | 100 | 100 | 100 |

The level of residual retinol after two months of storage at 50° C. in an aerobic medium (55 vol % air) is monitored by HPLC (same conditions as in Test 1).
The following results are obtained:

| Formula | Level of residual retinol |
|---|---|
| Formula A2 | 0% |
| Formula B2 | 83% |
| Formula C2 | 17% |
| Formula D2 | 27% |

Test 3: Influence of the neutralization of PEI with acetic acid

| Constituents | Formula A3 | Formula B3 | Formula C3 |
|---|---|---|---|
| All-trans-retinol Fluka (W/V) | 0.3% | 0.3% | 0.3% |
| PEI-700 Aldrich (W/V) | — | 1% | 1% |
| Acetic acid (W/V) | — | — | 1% |
| Absolute ethanol in ml | 100 | 100 | 100 |

The level of residual retinol after one month of storage at 50° C. in an aerobic medium (55 vol % air) is monitored by HPLC (same conditions as in Test 1).
The following results are obtained:

| Formula | Level of residual retinol |
|---|---|
| Formula A3 | 0% |
| Formula B3 | 91% |
| Formula C3 | 89% |

It is observed, by this test, that polyethyleneimine retains its activity as retinoid stabilizer regardless of the pH of the medium.

Test 4: Comparison of PEI and vitamin C:

| Constituents | Formula A4 | Formula B4 |
|---|---|---|
| All-trans-retinol Fluka (W/V) | 0.26% | 0.26% |
| PEI-700 Aldrich (W/V) | 0.1% | — |
| Ascorbic acid (W/V) | — | 0.25% |
| Absolute ethanol in ml | 100 | 100 |

From an alcoholic solution of retinol at 0.26%, the level of residual retinol after several days of storage of the formulae at 50° C. in aerobic medium (55 vol % of air) is monitored by HPLC.

The following results are obtained after 7 days of storage:

| Formula | Level of residual retinol |
|---|---|
| Formula A4 | 0.26% |
| Formula B4 | 0% |

Test 5: Comparison PEI and EDTA:

| Constituents | Formula A5 | Formula B5 |
|---|---|---|
| All-trans-retinol Fluka (W/V) | 0.26% | 0.26% |
| PEI-700 Aldrich (W/V) | 0.1% | — |
| EDTA (W/V) | — | 0.1% |
| Absolute ethanol in ml | 100 | 100 |

From an alcoholic solution of retinol at 0.26%, the level of residual retinol after several days of storage of the formulae at 50° C. in an aerobic medium (55 volt of air) is monitored by HPLC. The following results are obtained after 1, 2 and 5 days of storage:

|  | 1 day | 2 days | 5 days |
|---|---|---|---|
| Formula A5 | 0.23% | 0.23% | 0.22% |
| Formula B5 | 0.08% | 0.025% | 0% |

Test 6: Comparison PEI, spermine and spermidine:

| Constituents | Formula A6 | Formula B6 | Formula C6 |
|---|---|---|---|
| All-trans-retinol Fluka (W/V) | 0.3% | 0.3% | 0.3% |
| PEI-700 Aldrich (W/V) (*) | 0.25% | — | — |
| Spermine (*) | — | 0.25% | — |
| Spermidine (*) | — | — | 0.25% |
| Absolute ethanol in ml | 100 | 100 | 100 |

(*) compound neutralized at 75% with acetic acid

From an alcoholic solution of retinol at 0.3%, the level of residual retinol after several days of storage of the formulae at 50° C. in an aerobic medium (55 vol % of air) is measured by HPLC. This measurement is converted to level of degradation of retinol:

% degradation=([retinol $(T_0)$]−[retinol $(T_x)$])/[retinol $(T_0)$].

[retinol $(T_0)$] designates the initial concentration of retinol in the solution

[retinol $(T_x)$] designates the concentration of retinol in the solution at time $T_x$ The following results are obtained after 4, 14 and 21 days of storage:

|  | 4 days | 14 days | 21 days |
|---|---|---|---|
| Formula A6 | 1% | 4% | 7% |
| Formula B6 | 12% | 32% | 41% |
| Formula C6 | 16% | 40% | 50% |

All these tests show the superiority of polyethyleneimine in the stabilization of retinol compared with the products known until now as antioxidants or as retinoid stabilizers.

The disclosure of French priority application 9706533 filed May 28, 1997 is hereby incorporated by reference into the application.

Obviously, numerous modifications and variations of the present invention are possible in light of the above teachings. It is, therefore, to be understood that within the scope of the appended claims, the invention may be practiced otherwise than as specifically described herein.

What is claimed as new and is intended to be secured by Letters Patent is:

1. A composition comprising the combination of:
   (A) at least one retinoid selected from the group consisting of vitamin A and the bioconvertible precursors of vitamin A; and
   (B) at least one polyamine polymer selected from the group consisting of:
      (A) a polyalkylenepolyamine selected from the group consisting of:
         (i) alkylated polyalkylenepolyamines;
         (ii) products of addition of alkylcarboxylic acids to the polyalkylenepolyamines;
         (iii) products of addition of ketones and of aldehydes to the polyalkylenepolyamines;
         (iv) products of addition of isocyanates and of isothiocyanates to the polyalkylenepolyamines;
         (v) products of addition of alkylene oxide or of polyalkylene oxide block polymers to the polyalkylenepolyamines;
         (vi) quaternized derivatives of polyalkylenepolyamines;
         (vii) product of addition of a silicone to the polyalkylenepolyamines;
         (viii) a copolymer of dicarboxylic acid and polyalkylenepolyamines;
      (B) polyvinylimidazole;
      (C) polyvinylpyridines;
      (D) products of addition of 1-vinylimidazole monomers of formula (I):

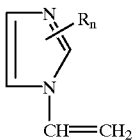

(I)

in which the R radicals, which are identical or different, represent H, or a linear or cyclic, saturated or unsaturated $C_1$–$C_6$ alkyl radical and n is an integer ranging from 1–3, to the polyalkylenepolyamines (A)(i) to (A)(viii);
      (E) polymers based on amino acids containing a basic side chain; and
      (F) cross-linked derivatives of the polymers (A)(i) to (A)(viii), (B) (C) (D) and (E).

2. The composition of claim 1, wherein the retinoid is selected from the Group consisting of retinol of the all-trans type and retinol of the 13-cis type.

3. The composition of claim 1, wherein the retinoid is selected from the group consisting of the retinol esters.

4. The composition of claim 3, wherein the retinoid is selected from the group consisting of the $C_1$–$C_6$ retinol esters.

5. The composition of claim 1, wherein the polyamine polymer is selected from polyamine polymers which contain at least 5% of tertiary amine functional groups.

6. The composition of claim 1, wherein the polyamine polymer is selected from the group consisting of:
   (A) (i) hyperbranched polyethyleneimines,
      (ii) quaternized polyethyleneimine;
      (iii) products of addition of alkylcarboxylic acids to polyethyleneimine;
      (iv) products of addition of ketones and of aldehydes to polyethyleneimine;
      (v) products of addition of isocyanates and of thioisocyanates to polyethyleneimine;
      (vi) products of addition of alkylene oxide or of polyalkylene oxide block polymers to polyethyleneimine;
      (vii) products of addition of a silicone to polyethyleneimine;
      (viii) a copolymer of dicarboxylic acid and of polyethyleneimine;
   (B) polyvinylimidazoles.

7. The composition of claim 1, wherein the polyamine polymer is selected from hyperbranched polyethyleneimines.

8. The composition of claim 1, which further comprises at least one sunscreening agent.

9. A cosmetic and/or dermatological composition, comprising a combination of the composition of claim 1 and a physiologically acceptable carrier.

10. The composition of claim 9, wherein the retinoid is present in a quantity ranging from 0.0001–10% by weight relative to the total weight of the composition.

11. The composition of claim 9, wherein the polyamine polymer is present in a quantity ranging from 0.001–20% by weight relative to the total weight of the composition.

12. The composition of claim 9, which further comprises at least one compound selected from the group consisting of chelating agents, polysaccharides, oils having an iodine number greater than or equal to 70, polyethylene glycol and/or polypropylene glycols, hydroxycarboxylates, amino acids and their salts, butylated hydroxytoluene, butylated hydroxyanisole, $\alpha$-, $\beta$-, $\gamma$- and $\delta$-tocopherols, nordihydrogaiaretin, propyl gallate, esters of fatty acids and of vitamin C, ascorbic acid, ascorbic acid salts, isoascorbic acid, isoascorbic acid salts, sorbic acid, sorbic acid salts, butanediol, fatty acid and pentaerythritol esters, fatty esters of trimethylolpropane, and hydrophilic mineral clays.

13. The composition of claim 9, which further comprises at least one specific anti-acne agent, one antiaeborrhoeic agent and/or one antibacterial agent.

14. The composition of claim 9, which is in the form of a lotion, a gel, a water-in-oil emulsion, an oil-in-water emulsion, a triple emulsion, nanocapsules, liposomes, nanoemulsions or oleosomes.

15. The composition of claim 9, which is in the form of a care cream, a milk, a tonic, a cleansing and/or make-up removing product, a pack, a peeling product, an exfoliating agent, a sun protection product, a foundation, a tinted cream or a lipstick.

16. A method of stabilizing a retinoid composition, comprising:
   combining a retinoid selected from the group consisting of vitamin A and the bioconvertible precursors of vitamin A and a least one polyamine polymer as defined in claim 1, thereby effectively stabilizing the retinoid against degradation.

17. A method of combating irritation, inflammation, immunosuppression and/or acne of the skin, comprising: treating the skin with the composition of claim 1.

18. A method of cosmetically treating the signs of ageing of the skin, the scalp, the hair or combinations thereof, comprising:

treating the skin, the scalp, the hair or combinations thereof with the composition of claim 9.

19. A method of combating the signs of ageing of the skin or of the hair, comprising:

treating the skin or hair with the cosmetic composition of claim 9.

20. The method of claim 19, wherein the ageing is a photoinduced ageing of the skin and/or of the hair.

21. A method of combating the signs of ageing of the skin or of the hair, comprising:

treating the skin or hair with the dermatological composition of claim 9.

22. A composition comprising the combination of:

(A) at least one retinoid selected from the group consisting of vitamin A and the bioconvertible precursors of vitamin A, and (B) alkylated polyalkylenepolyamines.

* * * * *

UNITED STATES PATENT AND TRADEMARK OFFICE
CERTIFICATE OF CORRECTION

PATENT NO.     : 6,344,206
DATED          : February 5, 2002
INVENTOR(S)    : Quang L. Nguyen et al.

It is certified that error appears in the above-identified patent and that said Letters Patent is hereby corrected as shown below:

<u>Column 15,</u>
Line 30, "product" should read -- products --;
Line 34, "polyvinylimidazole" should read -- polyvinylimidazoles --;
Line 58, "Group" should read -- group --.

<u>Column 16,</u>
Line 46, "antiaeborrhoeic" should read -- antiseborrhoeic --.

Signed and Sealed this

Twenty-first Day of May, 2002

*Attest:*

*Attesting Officer*

JAMES E. ROGAN
*Director of the United States Patent and Trademark Office*